(12) United States Patent
Garai

(10) Patent No.: US 11,792,714 B2
(45) Date of Patent: Oct. 17, 2023

(54) MEDICINE ADMINISTRATION IN DYNAMIC NETWORKS

(71) Applicant: Medtronic MiniMed, Inc., Northridge, CA (US)

(72) Inventor: Ellis Garai, Woodland Hills, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 310 days.

(21) Appl. No.: 17/348,871

(22) Filed: Jun. 16, 2021

(65) Prior Publication Data

US 2022/0408338 A1 Dec. 22, 2022

(51) Int. Cl.
| | |
|---|---|
| *G06F 15/173* | (2006.01) |
| *H04W 40/02* | (2009.01) |
| *A61M 5/315* | (2006.01) |
| *A61M 5/172* | (2006.01) |
| *H04L 67/12* | (2022.01) |
| *H04W 84/18* | (2009.01) |

(52) U.S. Cl.
CPC ............ *H04W 40/02* (2013.01); *A61M 5/172* (2013.01); *A61M 5/31568* (2013.01); *H04L 67/12* (2013.01); *A61M 2205/3561* (2013.01); *A61M 2205/3584* (2013.01); *A61M 2205/50* (2013.01); *A61M 2230/201* (2013.01); *H04W 84/18* (2013.01)

(58) Field of Classification Search
CPC ..... H04W 40/02; H04W 84/18; A61M 5/172; A61M 5/31568; A61M 2205/3561; A61M 2205/3584; A61M 2205/50; A61M 2230/201; H04L 67/12

USPC ........................................................ 709/242
See application file for complete search history.

(56) References Cited

U.S. PATENT DOCUMENTS

| | | | |
|---|---|---|---|
| 4,755,173 A | 7/1988 | Konopka et al. | |
| 5,391,250 A | 2/1995 | Cheney, II et al. | |
| 5,485,408 A | 1/1996 | Blomquist | |
| 5,522,803 A | 6/1996 | Teissen-Simony | |

(Continued)

FOREIGN PATENT DOCUMENTS

| | | | | |
|---|---|---|---|---|
| WO | WO-2018152349 A1 * | 8/2018 | ......... | A61B 5/14532 |
| WO | WO-2019004501 A1 * | 1/2019 | ............ | A61K 47/26 |

(Continued)

*Primary Examiner* — Alicia Baturay
(74) *Attorney, Agent, or Firm* — Carter, DeLuca & Farrell LLP

(57) ABSTRACT

Disclosed herein are techniques related to medicine administration in dynamic networks. The techniques may involve identifying an amount of medicine for delivery to a patient and determining a communication path toward a first medicine administration device of a plurality of medicine administration devices in a mesh network. The plurality of medicine administration devices may further include a second medicine administration device that is prioritized over the first medicine administration device for delivering medicine to the patient. The techniques may further involve causing delivery of the amount of medicine to the patient by the first medicine administration device based on communicating the amount of medicine toward the first medicine administration device via the communication path when the amount of medicine remains undelivered by the second medicine administration device.

20 Claims, 10 Drawing Sheets

(56) References Cited

U.S. PATENT DOCUMENTS

| | | |
|---|---|---|
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Nunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 9,233,204 B2 * | 1/2016 | Booth .................. G16H 80/00 |
| 9,323,893 B2 * | 4/2016 | Berry .................. G16H 40/67 |
| 9,407,624 B1 * | 8/2016 | Myers .................. H04W 12/04 |
| 9,504,789 B2 * | 11/2016 | Booth ............... A61B 5/14532 |
| 9,592,335 B2 * | 3/2017 | Yap .................. A61M 5/14244 |
| 9,629,901 B2 * | 4/2017 | Estes .................. A61K 38/26 |
| 9,841,014 B2 * | 12/2017 | Yap .................. F04B 51/00 |
| 9,883,801 B2 * | 2/2018 | Stump .................. G16H 50/30 |
| 9,888,337 B1 * | 2/2018 | Zalewski ............. H04W 76/14 |
| 9,894,471 B1 * | 2/2018 | Zalewski ............. H04W 76/14 |
| 9,898,585 B2 * | 2/2018 | Booth .................... A61P 3/10 |
| 9,901,305 B2 * | 2/2018 | Massey ............. A61B 5/14532 |
| 9,911,290 B1 * | 3/2018 | Zalewski ............ G06Q 20/327 |
| 9,965,595 B2 * | 5/2018 | Booth .................. G16H 40/67 |
| 10,038,992 B1 * | 7/2018 | Zalewski ............. H04W 4/80 |
| 10,039,496 B2 * | 8/2018 | Yarger .................. G08C 17/02 |
| 10,140,820 B1 * | 11/2018 | Zalewski ............ G06Q 30/0633 |
| 10,142,822 B1 * | 11/2018 | Zalewski ............ H02N 11/002 |
| 10,152,453 B1 * | 12/2018 | Matz .................... G06F 3/0482 |
| 10,169,544 B2 * | 1/2019 | Breton ................. G16Z 99/00 |
| 10,187,773 B1 * | 1/2019 | Zalewski ............ H04B 1/3833 |
| 10,188,325 B2 * | 1/2019 | Esenaliev ........... A61B 8/4227 |
| 10,252,145 B2 * | 4/2019 | Tran .................... G06V 40/28 |
| 10,332,615 B2 * | 6/2019 | Kovatchev ............. G16B 5/00 |
| 10,355,730 B1 * | 7/2019 | Zalewski ............ H04L 67/10 |
| 10,456,086 B2 * | 10/2019 | Breton ................. A61B 5/0205 |
| 10,463,789 B2 * | 11/2019 | Breton ................. A61B 5/4839 |
| 10,510,219 B1 * | 12/2019 | Zalewski ............ G06Q 20/327 |
| 10,573,134 B1 * | 2/2020 | Zalewski ............ G06Q 20/12 |
| 10,582,358 B1 * | 3/2020 | Zalewski ............ H04W 4/80 |
| 10,607,507 B2 * | 3/2020 | Connor ............... A61B 5/4866 |
| 10,638,981 B2 * | 5/2020 | Patek ................ A61B 5/14532 |
| 10,643,289 B2 * | 5/2020 | Ferro dos Santos ...................... A01K 11/006 |
| 10,667,795 B2 * | 6/2020 | Ensenaliev ........... A61B 5/4875 |
| 10,681,518 B1 * | 6/2020 | Zalewski ............ H04W 76/14 |
| 10,681,519 B1 * | 6/2020 | Zalewski ............ H04W 4/70 |
| 10,813,592 B2 * | 10/2020 | Massey ............. A61B 5/7207 |
| 10,834,562 B1 * | 11/2020 | Zalewski ............ H04W 76/10 |
| 10,835,727 B2 | 11/2020 | Montalvo et al. |
| 10,848,192 B2 * | 11/2020 | Zalewski ............ H02N 11/002 |
| 10,855,321 B2 * | 12/2020 | Zalewski ............ H04W 76/14 |
| 10,881,334 B2 * | 1/2021 | Facchinetti ........ A61B 5/14532 |
| 10,896,245 B2 * | 1/2021 | Crothall ............ A61M 5/14244 |
| 10,938,094 B2 * | 3/2021 | Jow .................... H01Q 1/2216 |
| 10,977,907 B1 * | 4/2021 | Zalewski ............ G06Q 30/0633 |
| 11,108,436 B1 * | 8/2021 | Kerselaers ........... H04B 5/0081 |
| 11,179,517 B2 * | 11/2021 | Patek .................. A61M 5/1723 |
| 11,195,388 B1 * | 12/2021 | Zalewski ............ G07G 1/0072 |
| 11,210,925 B1 * | 12/2021 | Kosecoff ............... G08B 21/24 |
| 11,270,784 B2 * | 3/2022 | Matz .................... G16H 40/67 |
| 11,288,933 B1 * | 3/2022 | Zalewski ............ G06Q 20/327 |
| 11,289,201 B2 * | 3/2022 | Breton .................. A61B 5/0017 |
| 11,296,750 B2 * | 4/2022 | Kerselaers ........... H04B 5/0093 |
| 11,309,088 B2 * | 4/2022 | Patek .................. G16H 50/70 |
| 11,315,393 B1 * | 4/2022 | Zalewski ............ G06Q 20/12 |
| 11,357,426 B2 * | 6/2022 | Tran .................... A61B 5/0006 |
| 11,381,271 B2 * | 7/2022 | Zalewski ............ H04W 76/14 |
| 11,417,179 B1 * | 8/2022 | Zalewski ............ G07G 1/0072 |
| 11,437,139 B2 * | 9/2022 | Bradley .............. G16H 40/67 |
| 11,546,955 B2 * | 1/2023 | Kench .................. H04W 76/14 |
| 11,552,995 B2 * | 1/2023 | Weiler .................. H04L 63/18 |
| 11,567,062 B2 * | 1/2023 | Kovatchev ........... G16H 40/67 |
| 11,605,882 B2 * | 3/2023 | Jow .................... H04B 5/0031 |
| 11,620,879 B2 * | 4/2023 | Zalewski ............ G06Q 30/0633 705/26.8 |
| 11,636,740 B2 * | 4/2023 | Zalewski ............ G06Q 30/0633 705/26.8 |
| 11,642,454 B2 * | 5/2023 | Chiu .................. A61M 5/16836 604/66 |
| 2007/0123819 A1 | 5/2007 | Mernoe et al. |
| 2009/0081951 A1 * | 3/2009 | Erdmann ............... G16H 40/63 455/41.2 |
| 2009/0112626 A1 * | 4/2009 | Talbot .................... G16H 40/67 600/300 |
| 2010/0160861 A1 | 6/2010 | Causey, III et al. |
| 2010/0162960 A1 * | 7/2010 | Moon .................... A01K 29/00 119/51.02 |

(56) References Cited

U.S. PATENT DOCUMENTS

| | | | |
|---|---|---|---|
| 2014/0349257 A1* | 11/2014 | Connor | G16H 20/60 |
| | | | 434/127 |
| 2014/0379358 A1* | 12/2014 | Chovanda | G16H 50/20 |
| | | | 705/2 |
| 2018/0096588 A1* | 4/2018 | Shabah | G06Q 10/06311 |
| 2019/0054246 A1* | 2/2019 | Ganton | A61M 5/31546 |
| 2019/0054247 A1* | 2/2019 | Dantsker | A61M 5/31553 |
| 2019/0054250 A1* | 2/2019 | Amschler | A61M 5/24 |
| 2019/0054251 A1* | 2/2019 | Pieronek | A61M 5/24 |
| 2019/0054252 A1* | 2/2019 | Amschler | A61M 5/24 |
| 2019/0379232 A1* | 12/2019 | Lemdiasov | H04B 5/0081 |
| 2020/0046268 A1* | 2/2020 | Patek | A61B 5/7275 |
| 2020/0129099 A1* | 4/2020 | Mi | A61B 5/0006 |
| 2020/0275864 A1* | 9/2020 | Heikenfeld | A61B 5/14532 |
| 2020/0327973 A1 | 10/2020 | Pryor et al. | |
| 2021/0000347 A1* | 1/2021 | Stump | A61B 5/02444 |
| 2021/0000424 A1* | 1/2021 | Massey | A61B 5/4839 |
| 2022/0022273 A1* | 1/2022 | Kosecoff | H04W 4/70 |
| 2022/0039699 A1* | 2/2022 | Esenaliev | A61B 5/1075 |
| 2022/0203029 A1* | 6/2022 | Breton | A61B 5/7275 |
| 2022/0392632 A1* | 12/2022 | Wang | G16H 50/30 |
| 2022/0395200 A1* | 12/2022 | Kovatchev | G16H 50/50 |
| 2023/0169468 A1* | 6/2023 | Ranieri | G16H 40/67 |
| | | | 705/2 |

FOREIGN PATENT DOCUMENTS

| | | | | |
|---|---|---|---|---|
| WO | WO-2019036656 A1 * | 2/2019 | | A61M 5/24 |
| WO | WO-2019036659 A1 * | 2/2019 | | A61M 5/24 |
| WO | WO-2019036660 A1 * | 2/2019 | | A61M 5/24 |
| WO | WO-2019036662 A1 * | 2/2019 | | A61M 5/24 |
| WO | WO-2019036668 A1 * | 2/2019 | | A61M 5/24 |
| WO | WO-2022081788 A1 * | 4/2022 | | |
| WO | WO-2022182709 A1 * | 9/2022 | | |
| WO | WO-2022182736 A1 * | 9/2022 | | |

* cited by examiner

MEDICINE ADMINISTRATION IN DYNAMIC NETWORKS

FIELD

The present disclosure relates to medicine administration systems and, more particularly, to dynamic networks for medicine administration.

BACKGROUND

Diabetes mellitus ("diabetes") is a metabolic disease that affects the regulation of glucose by insulin. Diabetes affects hundreds of millions of people and is among the leading causes of death globally. Diabetes has been categorized into three types: type 1, type 2, and gestational diabetes. Type 1 diabetes is associated with the body's failure to produce insulin. Type 2 diabetes is associated with the body's failure to produce sufficient amounts of insulin. Gestational diabetes is associated with insulin-blocking hormones that are produced during pregnancy. Gestational diabetes often resolves after pregnancy; however, in some cases, gestational diabetes develops into type 2 diabetes.

Treatment for various diseases and medical conditions, such as diabetes, typically involves administering doses of medicine. When administering a liquid medicine by injection, for example, an appropriate dosage may be set in a medicine delivery device (e.g., a syringe, a medicine delivery pen, or a pump) and dispensed therefrom. Regardless of the particular delivery device utilized for administering medicine, accurately tracking the medicine dosed can help avoid over-delivery and under-delivery.

SUMMARY

To the extent consistent, any of the aspects and features detailed herein can be utilized with any of the other aspects and features detailed herein in any suitable combination. Provided in accordance with aspects of the present disclosure is a processor-implemented method. The method includes identifying an amount of medicine for delivery to a patient and determining a communication path toward a first medicine administration device of a plurality of medicine administration devices in a mesh network. The plurality of medicine administration devices further includes a second medicine administration device that is prioritized over the first medicine administration device for delivering medicine to the patient. The method also includes when the amount of medicine remains undelivered by the second medicine administration device, causing delivery of the amount of medicine to the patient by the first medicine administration device based on communicating the amount of medicine toward the first medicine administration device via the communication path.

In some aspects of the present disclosure, the mesh network is a full mesh network.

In some others aspect of the present disclosure, the mesh network is a partial mesh network.

In some aspects of the present disclosure, the communication path includes a relay node that is communicatively coupled to the first medicine administration device via a different communication path.

In some aspects of the present disclosure, the first medicine administration device is an insulin infusion device and the second medicine administration device is an insulin injection device.

In some aspects of the present disclosure, determining the communication path includes determining that the first medicine administration device is connected to the mesh network.

In some aspects of the present disclosure, the method also includes prior to causing delivery of the amount of medicine, determining that the amount of medicine remains undelivered to the patient by the first medicine administration device.

Also provided in accordance with aspects of the present disclosure is a system including one or more processors and one or more processor-readable storage media. The one or more processor-readable storage media store instructions which, when executed by the one or more processors, cause performance of identifying an amount of medicine for delivery to a patient and determining a communication path toward a first medicine administration device of a plurality of medicine administration devices in a mesh network. The plurality of medicine administration devices further includes a second medicine administration device that is prioritized over the first medicine administration device for delivering medicine to the patient. The instructions, when executed by the one or more processors, also cause performance of when the amount of medicine remains undelivered by the second medicine administration device, causing delivery of the amount of medicine to the patient by the first medicine administration device based on communicating the amount of medicine toward the first medicine administration device via the communication path.

In some aspects of the present disclosure, the mesh network is a full mesh network.

In some other aspects of the present disclosure, the mesh network is a partial mesh network.

In some aspects of the present disclosure, the communication path includes a relay node that is communicatively coupled to the first medicine administration device via a different communication path.

In some aspects of the present disclosure, the first medicine administration device is an insulin infusion device and the second medicine administration device is an insulin injection device.

In some aspects of the present disclosure, determining the communication path includes determining that the first medicine administration device is connected to a mesh network.

In some aspects of the present disclosure, the one or more processor-readable storage media further store instructions which, when executed by the one or more processors, cause performance of prior to causing delivery of the amount of medicine, determining that the amount of medicine remains undelivered to the patient by the first medicine administration device.

Also provided in accordance with aspects of the present disclosure is one or more non-transitory processor-readable storage media storing instructions. The instructions, when executed by one or more processors, cause performance of identifying an amount of medicine for delivery to a patient and determining a communication path toward a first medicine administration device of a plurality of medicine administration devices in a mesh network. The plurality of medicine administration devices further includes a second medicine administration device that is prioritized over the first medicine administration device for delivering medicine to the patient. The instructions, when executed by the one or more processors, also cause performance of when the amount of medicine remains undelivered by the second medicine administration device, causing delivery of the amount of medicine to the patient by the first medicine administration device based on communicating the amount of medicine toward the first medicine administration device via the communication path.

In some aspects of the present disclosure, the mesh network is a full mesh network.

In some other aspects of the present disclosure, the mesh network is a partial mesh network.

In some aspects of the present disclosure, the communication path includes a relay node that is communicatively coupled to the first medicine administration device via a different communication path.

In some aspects of the present disclosure, the first medicine administration device is an insulin infusion device and the second medicine administration device is an insulin injection device.

In some aspects of the present disclosure, determining the communication path includes determining that the first medicine administration device is connected to the mesh network.

BRIEF DESCRIPTION OF DRAWINGS

The above and other aspects and features of the present disclosure will become more apparent in view of the following detailed description when taken in conjunction with the accompanying drawings wherein like reference numerals identify similar or identical elements.

DETAILED DESCRIPTION

Figure 1A:
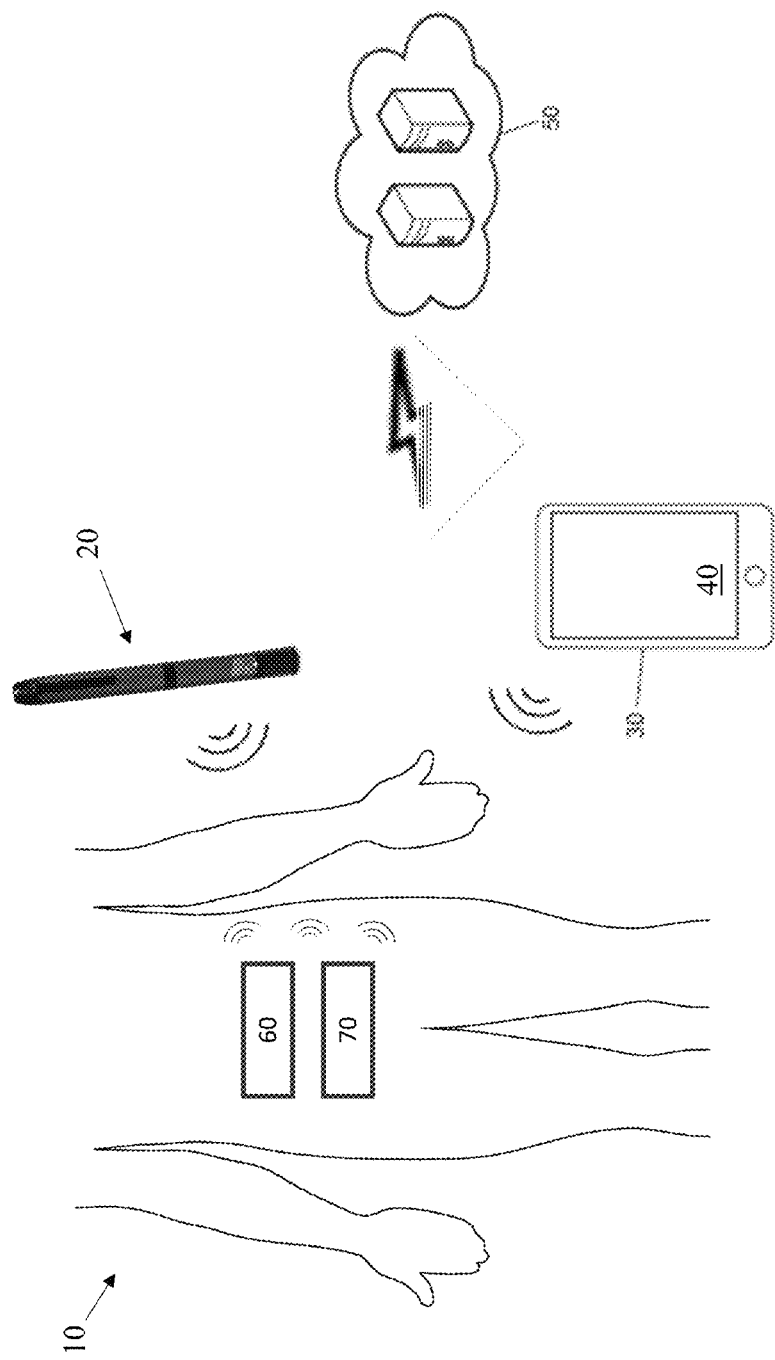
FIG. 1A is a schematic illustration of an example medicine administration and tracking system provided in accordance with the present disclosure including a medicine injection pen, a computing device, a medicine infusion device, and, in aspects, a sensor device and/or a data processing system.

The present disclosure relates to mesh networks for medicine administration. Various diseases and medical conditions, such as diabetes, require a person (e.g., a patient or a user) to self-administer doses of a fluid medication. Typically, when administering a fluid medication, the appropriate dose amount is set and dispensed using a medicine-administering device such as, e.g., a syringe, a pen, or a medicine infusion pump. These medicine-administering devices may be part of a medicine administering system that provides a person with the ability to manage his/her Medical condition utilizing a software application on his/her personal computing device (e.g., smartphone). The personal computing device may be in communication over a network with one or more of the aforementioned medicine-administering devices and with one or more sensor devices (e.g., a wearable continuous glucose monitor) that monitor a person's health metrics and/or physiological parameters. Based on information communicated over the network from a medicine-administering device concerning an administered dose of medicine (e.g., a dose amount and/or timestamp data associated with the dose) and/or health metric and physiological parameter data monitored by a sensor device, the software application is able to calculate and recommend a dose of medicine for the person to administer using any one of the medicine-administering devices.

As is typical with data networks, interruptions or slowdowns in communication between devices may occur, for example, when one or more devices are out-of-range, a device is removed from the network, and/or a device is added to the network. However, for a medicine administering system such as the one described above, maintaining communication between devices within the network enables dose tracking, logging, calculation, and communication of dose data so that doses are not missed, an incorrect dose (e.g., underdose or overdose) is not administered, and/or a dose is not inadvertently administered by multiple medicine-administering, devices. For example, some people over the course of injection-based therapy tend to interchangeably use a pen and a medicine infusion pump to administer medicine. This may result in overdosing if for example, a dose of medicine is administered using a pen and the dose is inadvertently repeated using a medicine infusion pump. Underdosing is also possible, for example, if a person forgoes administering a dose of medicine using a pen under the mistaken belief that the dose was already administered using a medicine infusion pump.

To avoid the aforementioned shortcomings, disclosed herein are mesh networks for medicine administration. Advantageously, mesh networks enable multiple paths of communication between devices in the network, thereby providing redundancy. Furthermore, communication paths can be dynamically adjusted, and devices can be dynamically added/removed without interrupting network communication, thereby providing seamless and reliable communication of data (e.g., timely and accurate dosing information) for those undergoing injection-based therapy.

FIG. 1A illustrates an example medicine administration and tracking system 10 provided in accordance with the present disclosure including a medicine injection pen 20 in wireless communication with a computing device 30 running a health management application 40 associated with pen 20 and/or other devices part of or connected to system 10. System 10, in aspects, further includes a data processing system 50, a sensor device 60, and/or a medicine infusion device 70. While the components of system 10 are detailed herein configured for use with respect to diabetes management, it is understood that the components of system 10 are also applicable to management of other diseases and medical conditions and/or for use with other medicine administration and tracking systems.

Medicine injection pen 20, described in greater detail below, may be a reusable injection pen configured to removably receive a medicine cartridge, e.g., a cartridge of insulin, for injecting a selected dose of insulin into a user and recording information concerning the injected dose of insulin, e.g., a dose amount and/or timestamp data associated with the dose.

Computing device 30 is detailed and illustrated herein as a smartphone, although any other suitable computing device may be provided such as, for example, a tablet, a wearable computing device (e.g., a smart watch, smart glasses, etc.), a laptop and/or desktop computer, a smart television, a network-based server computer, etc. Thus, solely to provide a clear example, computing device 30 is hereinafter referenced as smartphone 30.

Medicine infusion device 70, in aspects, may be a medicine delivery device (e.g., a portable device comprising an infusion pump and referenced herein simply as "medicine infusion pump") configured to be carried or worn by the user and, similar to medicine injection pen 20, may be configured to removably receive a medicine cartridge, e.g., a cartridge of insulin, for infusing a selected dose of insulin into a user (e.g., via connected tubing that provides a fluid path to/from the body of the user) and recording information concerning the infused dose of insulin, e.g., a dose amount and/or timestamp data associated with the dose. Medicine infusion device 70 includes a suitable user interface to enable the user to manually operate medicine infusion device 70 (e.g., to set a dose to be delivered to user), and/or medicine infusion device 70 may operate in a so-called "auto mode" in which medicine infusion device 70 automatically delivers medicine (e.g., insulin) to the user based on dose settings, the user's glucose levels (e.g., as detected by sensor device 60), and/or data received from other devices connected to system 10 (e.g., smartphone 30, pen 20, etc.) Since medicine infusion device 70 and medicine injection pen 20 both serve to deliver medicine to the user, some users may choose to utilize either medicine infusion device 70 or medicine injection pen 20, but not both. Still other users may choose to utilize medicine infusion device 70 and medicine injection pen 20 interchangeably to manage their medical condition. For example, a user may switch between using these devices over the course of a day, for a period of days depending upon a user's situation and/or needs (e.g., based on a user's travel plans), or may switch from one device to the other after extended periods of time (e.g., week, year, etc.). Regardless of the user's tendencies in using these medicine administering devices, aspects of the present disclosure provide for communication amongst the devices connected to system 10 to help ensure that the user does not over-deliver or under-deliver medicine into his/her body while using these medicine administering devices to manage his/her medical condition.

Smartphone 30 may be paired with pen 20 and/or medicine infusion device 70 although other suitable configurations are also contemplated. In aspects, the pairing of smartphone 30 with pen 20 and/or medicine infusion device 70 at least partially unlocks health management application 40 to enable the user to utilize some or all features of health management application 40, e.g., according to the user's prescription. Thus, the act of pairing can unlock and enable the functionality of health management application 40 and/or system 10 (including pen 20), while health management application 40 (and/or system 10) may provide only limited features in the absence of pairing with pen 20 and/or medicine infusion device 70.

Health management application 40 of smartphone 30, in aspects, can monitor and/or control functionalities of pen 20 and/or medicine infusion device 70. Application 40 may include one or more sets of instructions corresponding to a dose calculator module and/or decision support module that can cause calculation and recommendation of a dose of medicine for the user to administer using pen 20 and/or medicine infusion device 70. Health management application 40 may implement a user interface on the hardware of smartphone 30 to allow a user to manage health-related data. For example, health management application 40 can be configured to control some functionalities of pen 20 and/or medicine infusion device 70 and provide an interactive user interface to allow a user to manage settings of pen 20 and/or medicine infusion device 70 that can affect the functionality of system 10 (FIG. 1A). Smartphone 30 can additionally or alternatively be used to obtain, process, and/or display contextual data that can be used to relate to the health condition of the user, including the condition for which pen 20 and/or medicine infusion device 70 is used to treat. For example, smartphone 30 may be operable to track the location of the user; physical activity of the user including step count, movement distance and/or intensity, estimated calories burned, and/or activity duration; and/or interaction pattern of the user with smartphone 30. In aspects, health management application 40 can aggregate and process the contextual data to generate decision support outputs, e.g., on the user interface, to guide and aid the user in monitoring his/her condition, using pen 20, using medicine infusion device 70, and/or managing his/her behavior to promote treatment and better health outcomes.

In aspects, system 10 further includes a data processing system 50 in communication with pen 20, medicine infusion device 70, sensor device 60, and/or smartphone 30. Data processing system 50 can include one or more computing devices in a computer system and/or communication network accessible via the internet, e.g., including servers and/or databases in the cloud. System 10 can additionally or alternatively include sensor device 60 to monitor one or more health metrics and/or physiological parameters of the user. Examples of health metric and physiological parameter data monitored by sensor device 60 include analytes (e.g., glucose), heart rate, blood pressure, user movement, temperature, etc. Sensor device 60 may be a wearable sensor device such as a continuous glucose monitor (CGM) to obtain interstitial glucose measurements that are processed to produce continuous glucose values. For example, the CGM can include suitable electronics (e.g., a processor, a memory, a transceiver, and/or a battery or other suitable power source) for processing, storing, and/or causing display of the continuous glucose values for the user. Such continuous glucose values can be utilized by health management application 40, for example, for displaying health data, in dose calculation and/or decision support, etc.

Figure 1C:
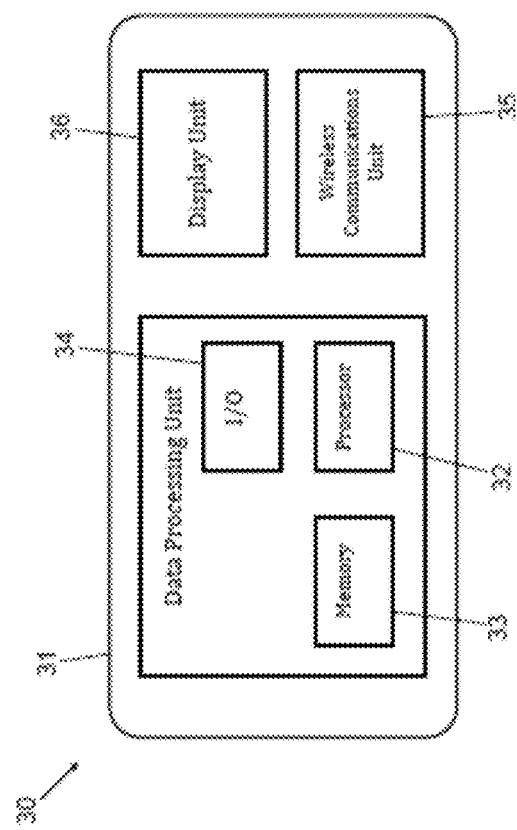
FIG. 1C is a block diagram of the computing device of the system of FIG. 1A.
Figure 1B:
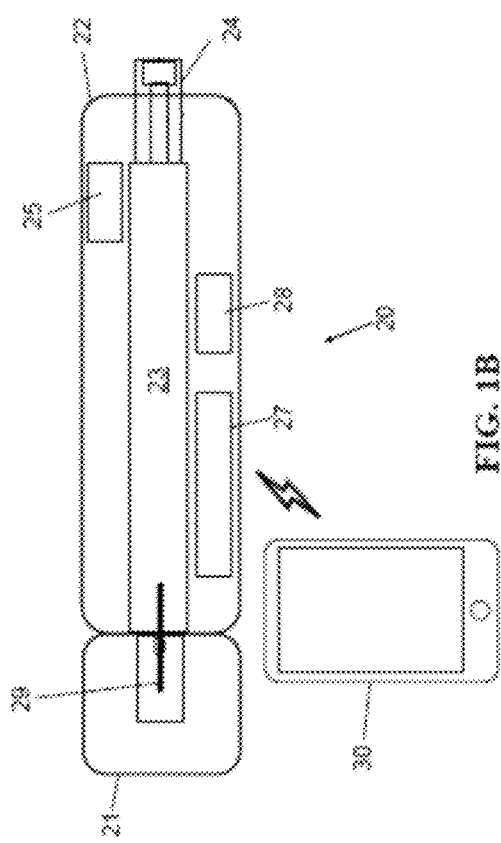
FIG. 1B is a block diagram of the medicine injection pen of the system of FIG. 1A.

With reference to FIG. 1B, pen 20 includes a cap 21 configured to protect a medicine dispensing element (e.g., a needle 29) and a body 22 configured to contain a replaceable medicine cartridge 23, e.g., an insulin cartridge. Pen 20 further includes a dose dispensing mechanism 24 to dispense (e.g., deliver) medicine contained in medicine cartridge 23 out of pen 20 (e.g., through needle 29); a dose setting mechanism 25 to enable the selection and/or setting of a dose of medicine to be dispensed; an operations monitoring mechanism 28 (e.g., including one or more switches, sensors (electrical, optical, acoustic, magnetic, etc.), encoders, etc.) to qualitatively determine that pen 20 is being operated and/or to monitor the operation of pen 20 (e.g., to quantitatively determine an amount of medicine set and/or dosed); and an electronics unit 27 that can include a processor, a memory, a transceiver, and a battery or other suitable power source.

In aspects, the memory of electronics unit 27 of pen 20 can store the amount of a dose along with a timestamp for that dose and/or any other information associated with the dose. In aspects, the transceiver of electronics unit 27 enables pen 20 to transmit the amount of the dose and related information to smartphone 30. In such aspects, once the amount of the dose is transmitted, the dose data and any related information associated with that particular dose may be marked as transmitted. If the dose is not yet transmitted to smartphone 30 such as, for example, because no connection between the pen 20 and smartphone 30 is available, then the dose data and any related information can be transmitted the next time a successful communication link between pen 20 and smartphone 30 is established.

In aspects, cap 21 is a so called "smart cap" configured to wirelessly communicate with pen 20 and smartphone 30 to transmit and/or track data related to operation of pen 20 regardless of whether cap 21 is attached or removed from pen 20. For example, cap 21 may include suitable electronics (e.g., similar to electronics unit 27 and/or operations monitoring mechanism 28) to enable transmission of the dose and related information from cap 21 to smartphone 30. Cap 21 may be configured to wirelessly communicate with other devices connected to system 10 such as data processing system 50, sensor device 60, and/or medicine infusion device 70.

FIG. 1C illustrates smartphone 30 of system 10 (FIG. 1A) including a data processing unit 31, a communications unit 35, and a presentation unit 36. Data processing unit 31 includes a processor 32 to process data, a memory 33 in communication with the processor 32 to store data, and an input/output unit (I/O) 34 to interface with other modules, units, and/or devices of smartphone 30 and/or external devices. Processor 32 can include a central processing unit (CPU) or a microcontroller unit (MCU). Memory 33 can include and store processor-executable code, which when executed by processor 32, configures the data processing unit 31 to perform various operations, e.g., such as receiving information, commands, and/or data, processing information and data, and transmitting or providing information/data to another device. In aspects, data processing unit 31 can cause transmission of raw or processed data to data processing system 50 (FIG. 1A). To support various functions of data processing unit 31, memory 33 can store information and data, such as instructions, software, values, images, and other data processed or referenced by processor 32. For example, various types of Random Access Memory (RAM) devices, Read Only Memory (ROM) devices, Flash Memory devices, and other suitable storage media can be used to implement storage functions of memory 33. I/O 34 of data processing unit 31 enables processing unit 31 to interface with communications unit 35 to utilize various types of wired or wireless interfaces (e.g., a wireless transmitter/receiver (Tx/Rx)) compatible with typical data communication standards to enable communication between data processing unit 31 and other devices such as pen 20. Examples of typical data communication standards include, but are not limited to, Bluetooth, Bluetooth low energy, Zigbee, IEEE 802.11, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), 3G/4G/LTE cellular communication methods, NFC (Near Field Communication), and parallel interfaces. I/O 34 of data processing unit 31 can also interface with other external interfaces, sources of data storage, and/or visual or audio display devices, etc. to retrieve and transfer data and information that can be processed by processor 32, stored in memory 33, and/or exhibited on an output unit of smartphone 30 and/or an external device. For example, presentation unit 36 of smartphone 30 can be configured to be in data communication with data processing unit 31, e.g., via I/O 34, to provide a visual presentation, an audio presentation, and/or other sensory presentation for implementing the user interface of the health management application 40 (FIG. 1A). In some examples, presentation unit 36 can include various types of screen displays, speakers, or printing interfaces, e.g., including but not limited to, LED, liquid crystal display (LCD) monitor or screen, cathode ray tube (CRT), audio signal transducer apparatuses, and/or toner, liquid inkjet, solid ink, dye sublimation, inkless (e.g., such as thermal or UV) printing apparatuses, etc.

Once smartphone 30 receives the dose data and related information (e.g., which can include time information; dose setting and/or dose dispensing information; and/or other information about pen 20, medicine infusion device 70, and/or the environment as it relates to a dosing event), smartphone 30 stores the dose related information, which can be included among a list of doses or dosing events. In aspects, via the user interface associated with health management application 40, smartphone 30 allows the user to browse a list of previous doses, to view an estimate of current medicine active in the patient's body (medicine-on-board, e.g., insulin-on-board) based on calculations performed by health management application 40. Additionally or alternatively, smartphone 30 may allow the user to utilize a dose calculation module to assist the patient regarding dose setting information (e.g., the size of the next dose(s) to be delivered). For example, the patient may enter carbohydrates to be eaten, and health management application 40 may recommend a dosage based on insulin-on-board information. In aspects, smartphone 30 can also allow the user to manually enter dose data, e.g., boluses, which may be useful if the battery in pen 20 and/or medicine infusion device 70 has been depleted or another medicine delivery device, e.g., a syringe, was utilized to dose.

In aspects, system 10 may further include any one or more peripheral devices, referenced generally as 80 in FIGS. 2A, 2B, and 4-6. In aspects, peripheral device 80 may be an additional sensor device such as a blood glucose meter (BGM) used to determine a user's blood glucose based on processing of a blood sample. Use of a BGM involves the user pricking his/her finger to obtain the blood sample, which is applied onto a strip that is inserted into the BGM and processed to produce a blood glucose value. The BGM can include suitable electronics (e.g., a processor, a memory, a transceiver, and/or a battery or other suitable power source) for processing, storing, and/or causing display of blood glucose values for the user. Such blood glucose values can be utilized by health management application 40, for example, for displaying health data, in dose calculation and/or decision support, etc. Including an optional BGM in system 10 allows, for example, the user to calibrate sensor device 60 by comparing glucose levels measured by sensor device 60 to a blood glucose value produced by the BGM.

In aspects, peripheral device 80 may be any suitable computing device, examples of which include, but are not limited to, a laptop, a tablet computing device, and a smartwatch. Peripheral device 80 may include suitable sensor devices configured to monitor one or more health metrics and/or physiological parameters of the user. Examples of health metric and physiological parameter data that can be monitored by peripheral device 80 include analytes (e.g., glucose), heart rate, blood pressure, user movement, user consumption habits via gesture sensing, temperature, therapy information, carbohydrates consumption, etc.

In aspects, peripheral device 80 may be a wearable sensor device such as a smartwatch having a suitable sensor (e.g., optical sensor) to obtain glucose measurements that are processed to produce continuous glucose values. For example, peripheral device 80 may include suitable electronics (e.g., a processor, a memory, a transceiver, and a battery or other suitable power source) for processing, storing, and causing display of the continuous glucose values for the user. Such continuous glucose values can be utilized by health management application 40, for example, for displaying health data, in dose calculation and/or decision support, etc.

Referring generally now to FIGS. 2-6, various wireless network configurations to facilitate communication between devices connected to system 10 are shown. In some aspects, system 10 may be configured as a partial mesh wireless network in which less than all nodes are directly connected to each other node in the network. In such a network, one or more devices may serve as a relay node for communication between two or more other devices in system 10.

In some other aspects, system 10 may be configured as a full mesh network. In a full mesh network topology, each node is directly connected to each other node so that all node devices have multiple paths for communication to other node devices. In aspects, system 10 may be configured for communication through the mesh networking standard known in the art as Bluetooth® mesh networking to facilitate communication between node devices using Bluetooth low energy radio signals.

In aspects, new or previously unconnected devices may be introduced into the network of system 10 using a suitable wireless data communication standard, such as Bluetooth, in which the unconnected device operates in an advertising mode to transmit a data signal to establish bi-directional communication with one or more other devices connected to system 10, as is known in the art.

Figure 2A:
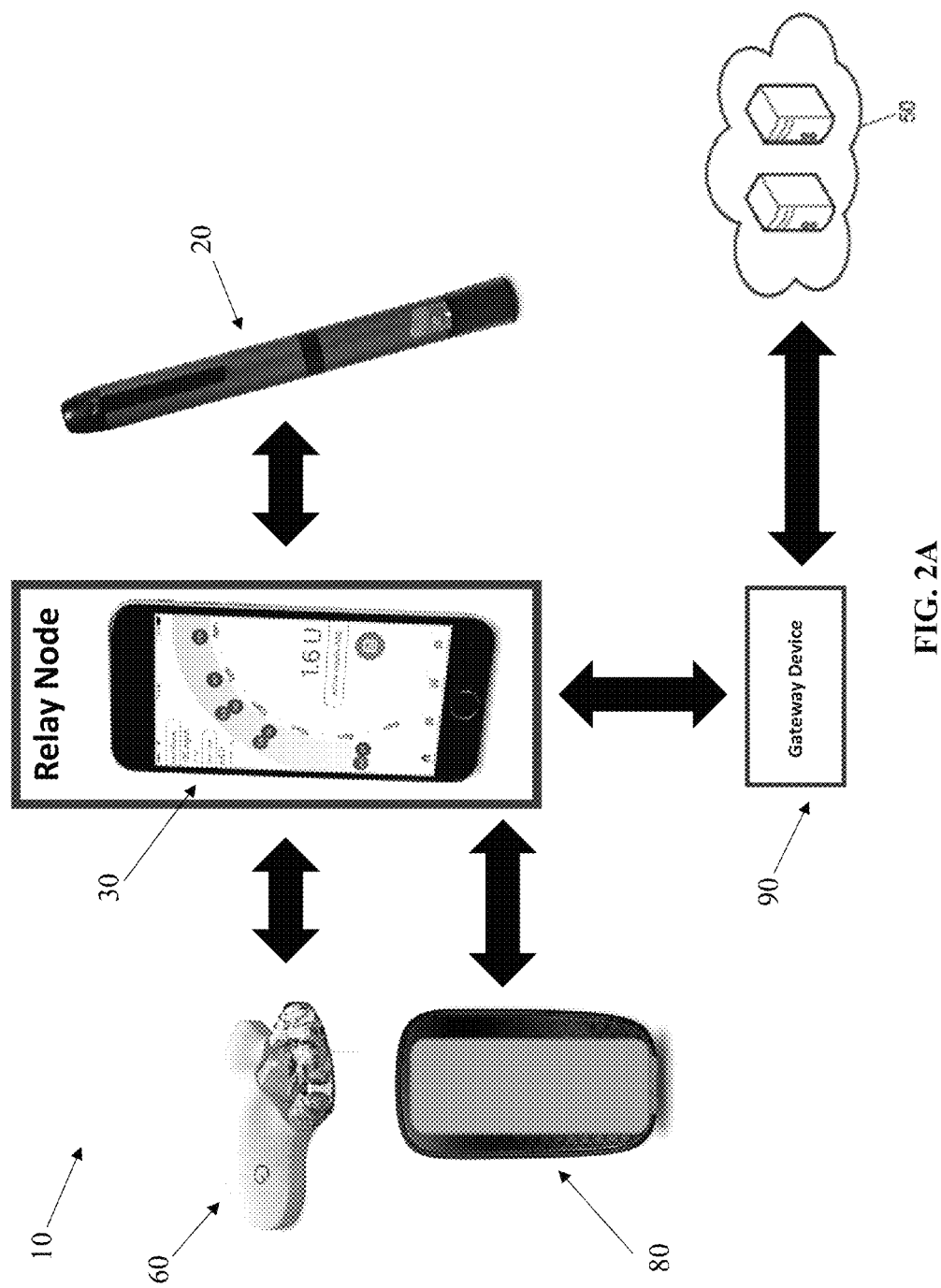
FIG. 2A illustrates the system of FIG. 1A arranged in a partial mesh communication network with the computing device acting as a relay node and including an optional peripheral device in accordance with aspects of the present disclosure.
Figure 2B:
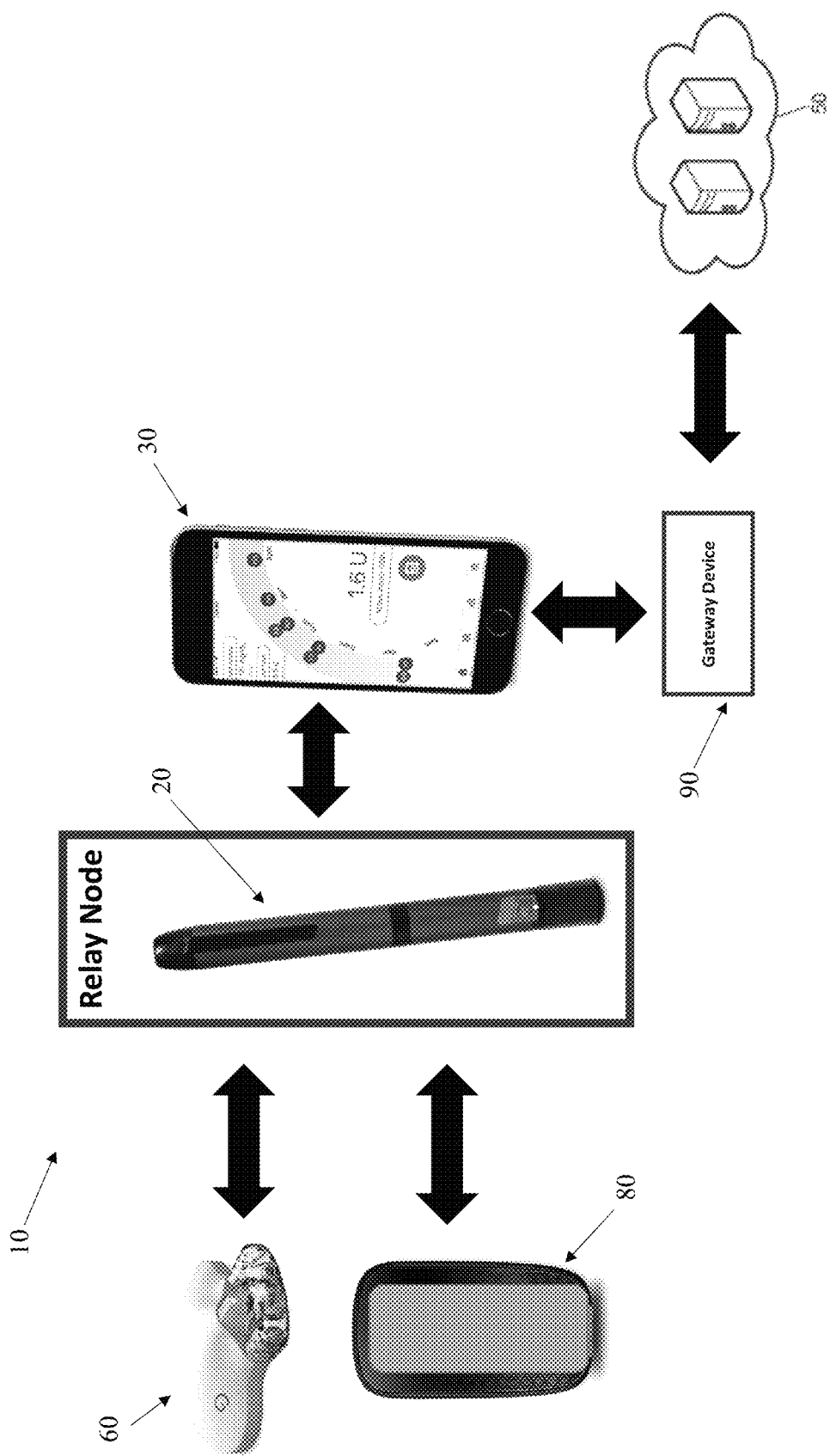
FIG. 2B illustrates the system of FIG. 1A arranged in a partial mesh communication network with the medicine injection pen acting as a relay node and including an optional peripheral device in accordance with aspects of the present disclosure.

Referring now to FIGS. 2A and 2B, the devices connected to system 10 are configured, in aspects, to communicate over a partial mesh wireless network in which either smartphone 30 (FIG. 2A) or pen 20 (FIG. 2B) serves as a relay node. As used herein, a relay node may correspond to any device that enables communication between nodes that are otherwise incapable of communicating with each other. With smartphone 30 serving as the relay node, as shown in FIG. 2A, data may be communicated from a first node device (e.g., pen 20, sensor device 60, or peripheral device 80) to smartphone 30 for further communication to a second node device (e.g., pen 20, sensor device 60, or peripheral device 80). With pen 20 serving as the relay node instead of smartphone 30, as shown in FIG. 2B, data may be communicated from a first node device (e.g., smartphone 30, sensor device 60, or peripheral device 80) to pen 20 for further communication to a second node device (e.g., smartphone 30, sensor device 60, or peripheral device 80). Thus, a relay node may extend the communication range. For example, in FIG. 2B, pen 20 may be within range of smartphone 30, and sensor device 60 may not be within range of smartphone 30. However, smartphone 30 may communicate with sensor device 60 via pen 20, which serves as a relay node.

In the examples of FIGS. 2A-B, each of the partial mesh networks is communicatively coupled to a gateway device 90 in communication with data processing system 50. Thus, data communicated to smartphone 30 may be processed by health management application 40 and optionally uploaded to data processing system 50 via gateway device 90.

Figure 3:
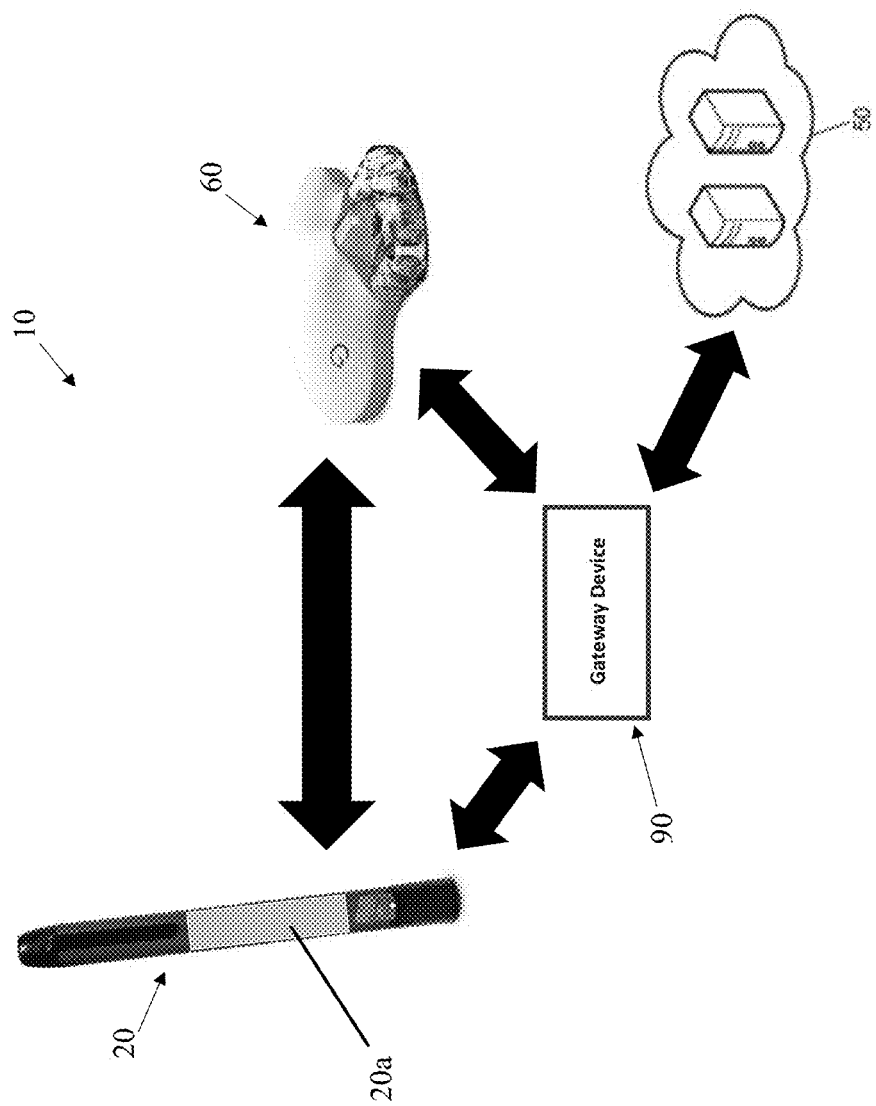
FIG. 3 illustrates the medicine injection pen and the sensor device of the system of FIG. 1A arranged in a full mesh communication network in accordance with aspects of the present disclosure.

Referring now to FIG. 3, smartphones and/or networks required to support use of smartphones may not be accessible and/or affordable to all users of system 10. With this scenario in mind, or for other purposes, the configuration of system 10 shown in FIG. 3 facilitates communication between devices connected to system 10 without smartphone 30. The configuration of FIG. 3 allows pen 20 and/or sensor device 60 to communicate directly with each other (and optionally peripheral device 80) and directly with gateway device 90 in communication with data processing system 50. Pen 20 may include a user interface 20a that operates substantially similar to display unit 36 of smartphone 30, as described above, to provide a visual display.

Figure 4A:
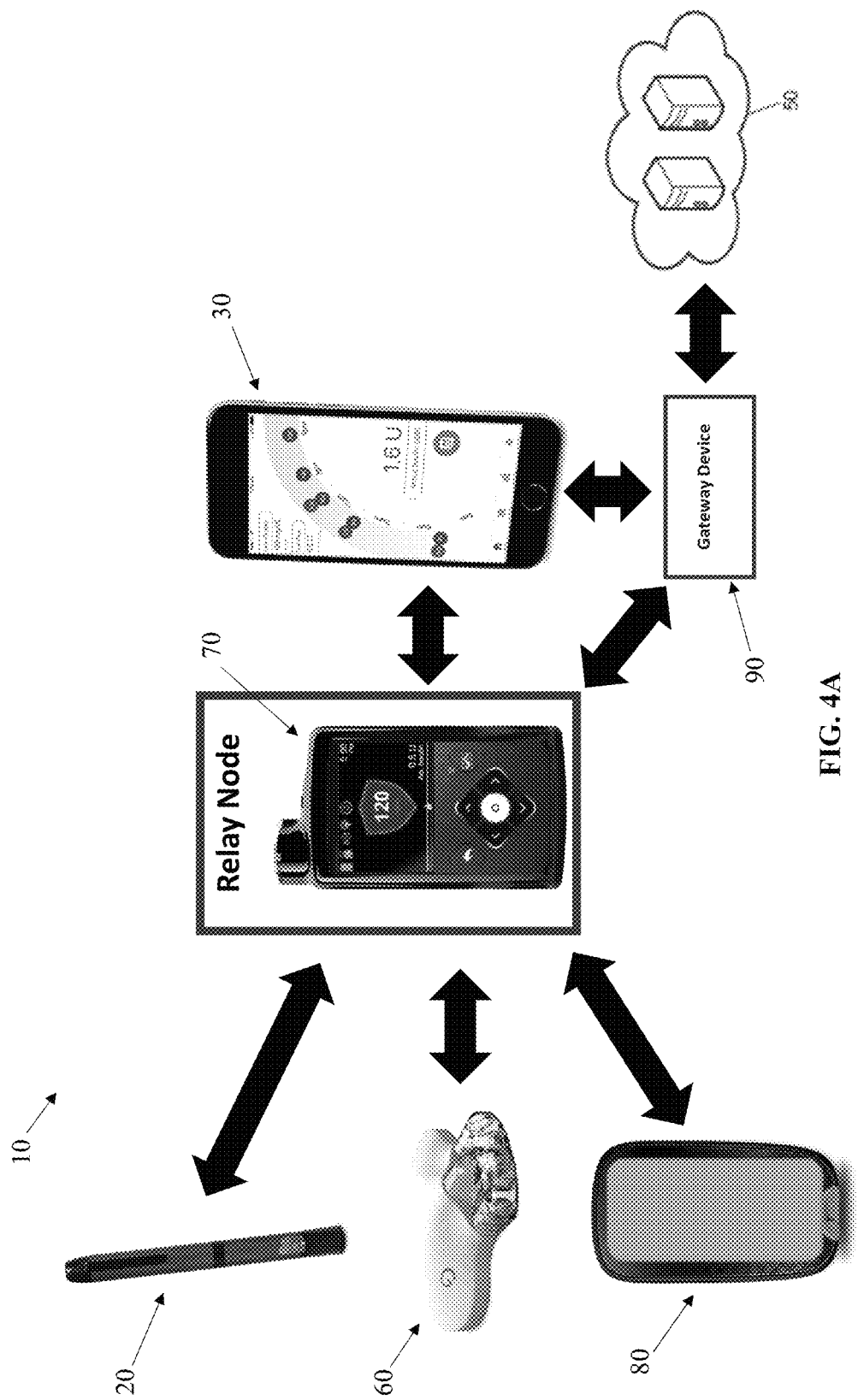
FIG. 4A illustrates the system of FIG. 1A arranged in a partial mesh communication network with the medicine infusion device acting as a relay node and including an optional peripheral device in accordance with aspects of the present disclosure.
Figure 4B:
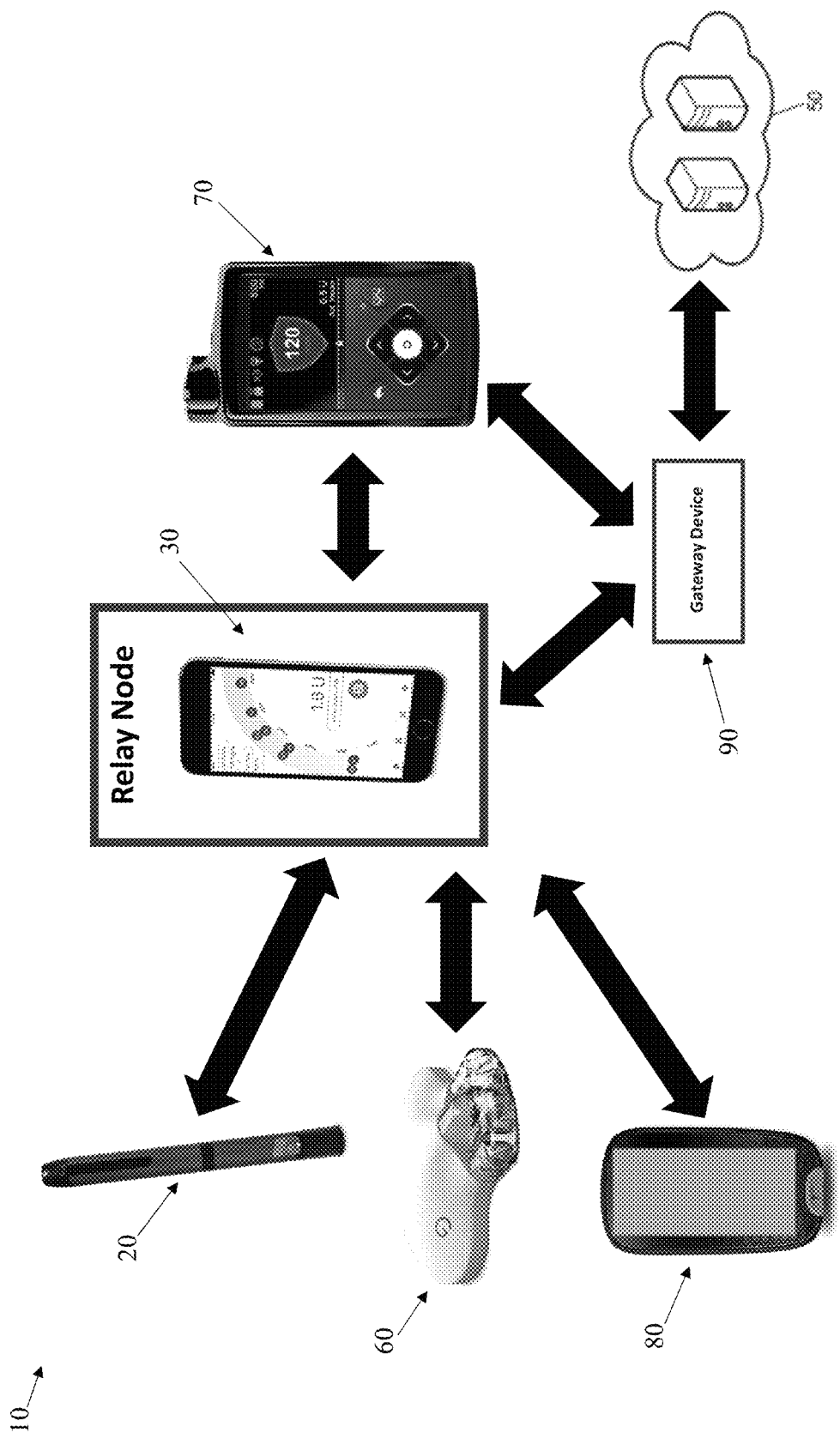
FIG. 4B illustrates the system of FIG. 1A arranged in a partial mesh communication network with the computing device acting as a relay node and including an optional peripheral device in accordance with aspects of the present disclosure.
Figure 5:
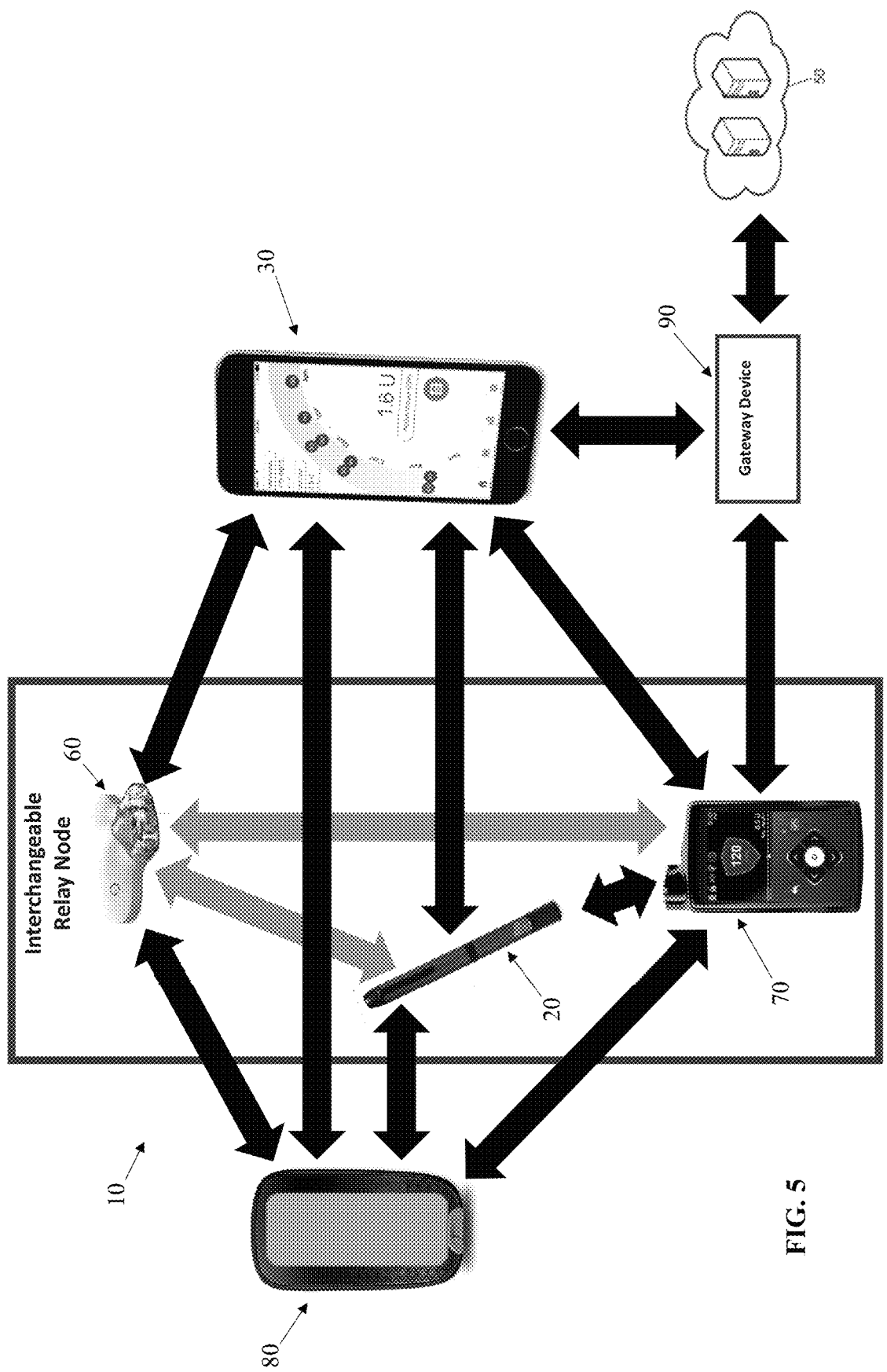
FIG. 5 illustrates the system of FIG. 1A arranged in a partial mesh communication network with the sensor device, the medicine infusion device, and the medicine injection pen interchangeably acting as a relay node and including an optional peripheral device in accordance with aspects of the present disclosure.
Figure 6:
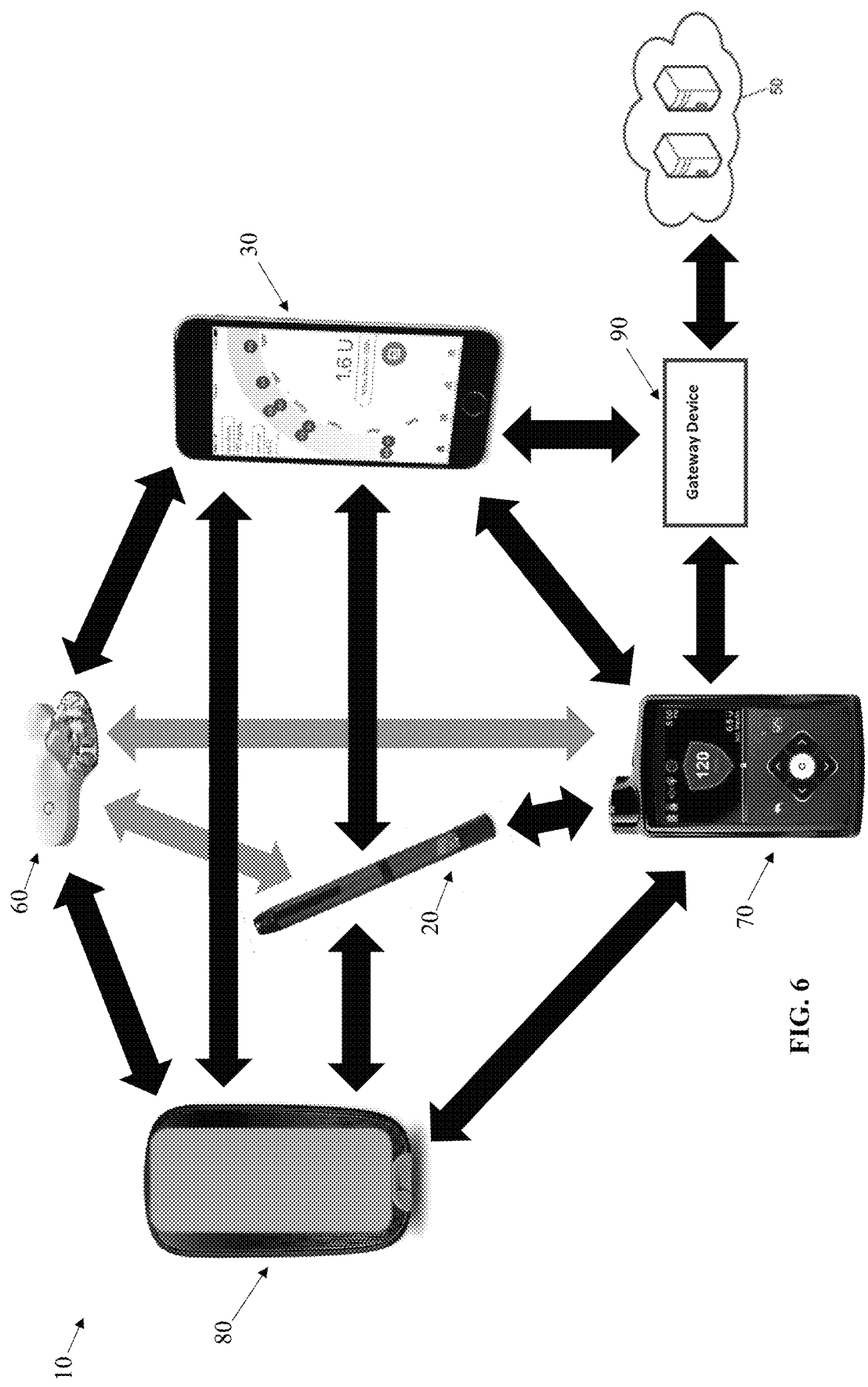
FIG. 6 illustrates the system of FIG. 1A arranged in a full mesh network and including an optional peripheral device in accordance with aspects of the present disclosure.

Referring generally to FIGS. 4-6, some users of medicine administering systems (e.g., system 10) tend to utilize a medicine injection pen (e.g., pen 20) in combination with other connected devices (e.g., smartphone 30, sensor device 60, etc.) to administer medicine and manage their medical condition. Some other users tend to utilize a medicine infusion device (e.g., medicine infusion device 70) in combination with other connected devices to administer medicine and manage their medical condition. Some other users tend to utilize a medicine injection pen and a medicine infusion device interchangeably in combination with other connected devices to administer medicine and manage their medical condition. FIGS. 4A-B provides various wireless network configurations to facilitate communication between devices connected to system 10 including pen 20 and medicine infusion device 70, thereby enabling pen 20 and medicine infusion device 70 to be utilized by the user interchangeably within system 10. This enables a user to administer medicine with either device and accurately track the amount of medicine delivered (e.g., and, thus, enable determination of insulin-on-board) to help ensure medicine is not over-delivered or under-delivered to the user. To the extent consistent and not explicitly contradicted below, any of the aspects and features detailed below with respect to any of the configurations of FIGS. 4-6 can be utilized, in whole or in part, in any suitable combination to achieve a particular purpose.

Referring now to FIGS. 4A and 4B, the devices connected to system 10 are configured, in aspects, to communicate over a partial mesh wireless network in which either medicine infusion device 70 (FIG. 4A) or smartphone 30 (FIG. 4B) serves as a relay node. With medicine infusion device 70 serving as the relay node, as shown in FIG. 4A, data may be communicated from a first node device (e.g., pen 20, smartphone 30, sensor device 60, or peripheral device 80) to medicine infusion device 70 for further communication to a second node device (e.g., pen 20, smartphone 30, sensor device 60, or peripheral device 80). With smartphone 30 serving as the relay node, as shown in FIG. 4B, data may be communicated from a first node device (e.g., pen 20, sensor device 60, medicine infusion device 70, or peripheral device 80) to smartphone 30 for further communication to a second node device (e.g., pen 20, sensor device 60, medicine infusion device 70, or peripheral device 80). Thus, a relay node may extend the communication range.

In the examples of FIGS. 4A-B, each of the partial mesh networks is communicatively coupled to gateway device 90 in communication with data processing system 50. Thus, data communicated to smartphone 30 may be processed by health management application 40 and optionally uploaded to data processing system 50.

Medicine infusion device 70 may serve as the relay node of system 10 regardless of whether it is being used for medicine administration or not. For example, a user may choose to utilize pen 20 for medicine delivery but still utilize medicine infusion device 70 as a relay node to facilitate communication between pen 20 and the other devices connected to system 10 (e.g., smartphone 30, sensor device 60, peripheral device 80, etc.).

Referring now to FIG. 5, the devices connected to system 10 are configured, in aspects, to communicate over a partial mesh wireless network in which multiple devices can interchangeably serve as a relay node. As illustrated in FIG. 5, for example, sensor device 60, pen 20, and medicine infusion device 70 may each serve as a relay node. As described in greater detail below, data may be communicated via a particular relay node based on various factors. In the example of FIG. 5, the partial mesh network is communicatively coupled to gateway device 90 in communication with data processing system 50. Thus, data communicated to smartphone 30 may be processed by health management application 40 and optionally uploaded to data processing system 50.

In aspects of the configuration shown in FIG. 5, one or more active devices of system 10 may serve as one or more relay nodes. For example, if the user is using pen 20 to deliver medicine, then pen 20 may serve as a relay node; if the user is using medicine infusion device 70 to deliver medicine, then medicine infusion device 70 may serve as a relay node; and if the user is manually injecting medicine using a syringe or disposable insulin pen, then sensor device 60 may serve as a relay node. Thus, communication paths can be dynamically adjusted in a seamless manner.

In aspects, a node can be dynamically added or removed in a seamless manner. For example, a node can be added based on operating in an advertising mode (e.g., via Bluetooth) and being detected by another device connected to system 10 (e.g., smartphone 30) to establish bi-directional communication. Thus, devices can connect to system 10 and disconnect from system 10 without interrupting communication between nodes.

In aspects, multiple devices may be available (e.g., active) to serve as a relay node. In such aspects, a particular relay node may be selected based on prioritization of candidate relay nodes. For example, if sensor device 60, pen 20, and medicine infusion device 70 are all available to serve as a relay node, then the available devices may be prioritized as follows: medicine infusion device 70 may have high priority, pen 20 may have intermediate priority, and sensor device 60 may have low priority.

In aspects, prioritization may be determined based on when a particular device joined the network. For example, the foregoing prioritization may be the result of device 70 joining the network before pen 20, which joined the network before device 60.

Additionally or alternatively, prioritization may be based on other factors such as, for example, available battery life of the devices (e.g., to prioritize devices with the most available battery), quality of service (e.g., to prioritize devices with the highest bandwidth and lowest latency), signal strength of connection (e.g., to prioritize devices that have the strongest signal), and/or for other reasons.

Referring now to FIG. 6, the devices connected to system 10 are configured to communicate over a full mesh network according to aspects of the present disclosure. The configuration of FIG. 6 may not use any hierarchical relationships (e.g., a relay node and peripheral nodes) but, rather, any device connected to system 10 may communicate (or attempt to communicate) with any other device connected to system 10 either directly or by daisy-chaining through any one or more other connected devices of system 10 to reach a destination device. The path (e.g., route) of communication from a source device to a destination device may be dynamically created and modified if the environment changes (e.g., a device disconnects from system 10, a new device connects to system 10, the device(s) operating in advertising mode changes, a device is out of range, low signal strength is detected, a device is deactivated, there are changes in data traffic, etc.). The ability to dynamically create and modify communication paths (e.g., routes) of the mesh network configuration of FIG. 6 increases the reliability of data connections between the devices connected to system 10. Additionally, any connected device can disconnect from the mesh network without interrupting communication between other devices connected to system 10. If a connected device (e.g., sensor device 60) is unable to communicate with another connected device (e.g., medicine infusion device 70) using a particular path (e.g., a previously established route), communication between the connected devices may proceed (e.g., based on flooding or dynamic rerouting) through any one or more other connected devices in the mesh network. For example, sensor device 60 may be unable to communicate directly with smartphone 30 due to a weak signal and/or a slow data transmission rate caused by smartphone 30 being out of range of sensor device 60. By leveraging its ability to communicate with any device connected to system 10, sensor device 60 can communicate with smartphone 30 by daisy chaining other connected devices, such as peripheral device 80 and medicine infusion device 70, to establish a path, albeit an indirect path, from sensor device 60 to smartphone 30. If, for example, medicine infusion device 70 disconnects from the mesh network, communication from sensor device 60 to smartphone 30 can proceed by daisy chaining other connected devices, such as peripheral device 80 and pen 20.

In aspects, system 10 may utilize what is known in the art as Received Signal Strength Indicator (RSSI) to dynamically route data communication. RSSI is an estimated measurement of a device's ability to detect and/or receive signals from another device to determine if a signal is sufficient to establish a connection for communication of data. Typically, the larger the distance between the devices attempting to communicate, the weaker the signal and the slower the data transmission. System 10 can, at each device along a communication route, determine which next device has the highest RSSI value and forward communication to that next device until a communication ultimately reaches its destination. In this way, communication routes may be established utilizing as many devices as necessary but as few devices as possible to create the most efficient route between devices.

In aspects, any of the devices of system 10 may include suitable electronics (e.g., a processor, a memory, a transceiver, and a battery or other suitable power source) so that, in the event that a data connection cannot be established with another device (e.g., smartphone 30), data can be continuously backed up to the device's memory (e.g., dose data including a dose timestamp and/or any other information associated with the dose) for a suitable period of time (e.g., 1 hour, 1 day, etc.) at least until the next time a successful communication link is established with another device such that the stored data can then be transmitted.

Figure 7:
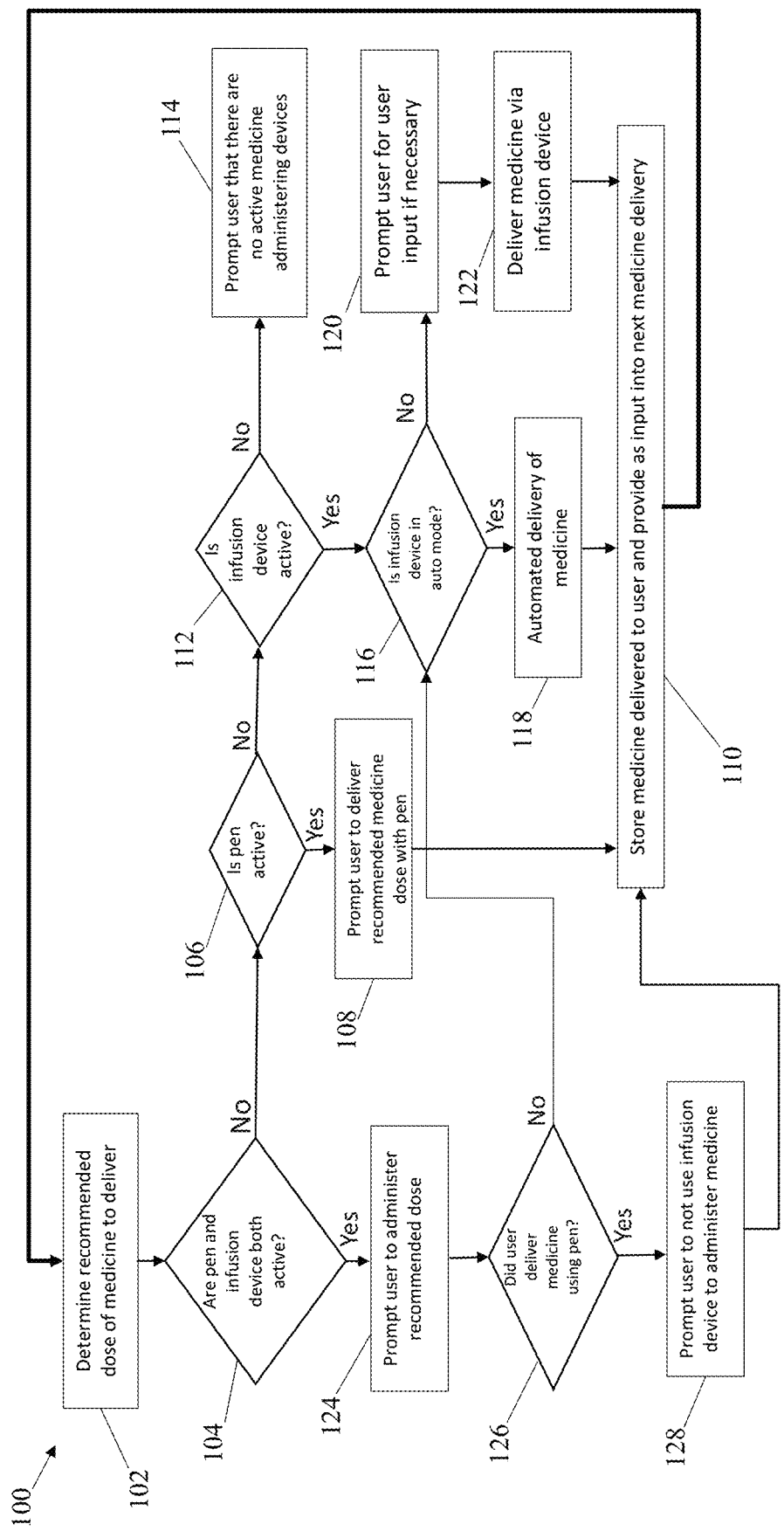
FIG. 7 is a flowchart illustrating an example approach for tracking and/or administering medicine using system of FIG. 1A in accordance with aspects of the present disclosure.

Turning now to FIG. 7, an example approach 100 is shown for enabling a user to utilize a medicine injection pen (e.g., pen 20 (FIG. 1A)) and a medicine infusion pump (e.g., medicine infusion device 70 (FIG. 1A)) interchangeably to deliver medicine to his/her body while ensuring the user does not over-deliver medicine (e.g., by mistakenly using both devices to deliver medicine) or under-deliver medicine (e.g., by failing to use any device to deliver medicine. Although the example approach 100 is described in terms of pen 20 and medicine infusion device 70, it should be appreciated that these devices are merely provided as examples and that other approaches may involve different combinations of devices.

At block 102, a recommended dose of medicine is calculated for the user to deliver (e.g., via a dose determination module). Dose recommendations may be presented to the user on the user interface provided by health management application 40 on smartphone 30.

Blocks 104, 106, and 112 depict an example approach for determining whether any medicine delivery devices are active (e.g., connected to the network and/or otherwise capable of medicine delivery). Although the example approach 100 is described in terms of pen 20 being prioritized over medicine infusion device 70, it should be appreciated that other approaches may employ different prioritizations. Furthermore, it should be appreciated that other approaches may determine whether any medicine delivery device are active in a different order and/or using more/fewer operations. For example, block 104 may be performed after block 112 or omitted entirely.

At block 104, a determination is made as to whether both pen 20 and medicine infusion device 70 are active. For example, health management application 40 may cause smartphone 30 to transmit a test communication (e.g., a ping) to each device and listen for a response from each device.

If, at block 104, it is determined that both pen 20 and medicine infusion device 70 are not active, it is determined at block 106 if pen 20 is active. If pen 20 is active the user is prompted at block 108 (e.g., via smartphone 30, via medicine infusion device 70, and/or via pen 20) to deliver the recommended dose of medicine using pen 20, and the amount of the dose delivered to the user and related information are transmitted to smartphone 30 and stored in memory 33 at block 110. Block 110 may proceed to block 102, and a recommended medicine dose may be calculated in view of, among other input parameters, the amount of the dose delivered to the user as stored in memory 33 at block 110.

If, at block 106, pen 20 is determined to not be active, it is determined if medicine infusion device 70 is active at block 112. If medicine infusion device 70 is determined to not be active, the user is prompted (e.g., via smartphone 30, via medicine infusion device 70, and/or via pen 20) that there are no active medicine administering devices at block 114. If, at block 112, medicine infusion device 70 is determined to be active, it is determined if medicine infusion device 70 is operating in auto mode at block 116. If medicine infusion device 70 is determined to be operating in auto mode, the recommended medicine dose is delivered automatically by medicine infusion device 70 at block 118, and the amount of the dose delivered to the user and related information are transmitted to smartphone 30 and stored in memory 33 at block 110.

Returning now to block 116, if it is determined that medicine infusion device 70 is not operating in auto mode, the user is prompted at block 120 (e.g., via smartphone 30, via medicine infusion device 70, and/or via pen 20) to manually input information (e.g., a dose setting) into medicine infusion device 70, if necessary, before operating medicine infusion device 70 to deliver medicine at block 122. The amount of the dose delivered to the user and related information are transmitted to smartphone 30 and stored in memory 33 at block 110.

Returning now to block 104, if it is determined that both pen 20 and medicine infusion device 70 are active, the user is prompted (e.g., via smartphone 30, via medicine infusion device 70, and/or via pen 20) to deliver the recommended dose of medicine at block 124. The user may choose to deliver medicine via pen 20 or via medicine infusion device 70.

At block 126, if it is determined that the user has not delivered medicine via pen 20, it is determined at block 116 if medicine infusion device 70 is operating in auto mode. Whether or not the user has delivered medicine via pen 20 may be determined based on communication between pen 20 and smartphone 30. For example, as long as smartphone 30 has not received a transmission from pen 20 including information relating to a dose delivered to the user via pen 20, a determination may be made that the user has not delivered medicine via pen 20. If smartphone 30 receives a transmission from pen 20 including information relating to a dose delivered to the user via pen 20, a determination may be made that the user delivered medicine via pen 20.

If it is determined at block 126 that the user has delivered medicine via pen 20, the user is prompted at block 128 (e.g., via smartphone 30, via medicine infusion device 70, and/or via pen 20) to not use medicine infusion device 70 to administer medicine, and the amount of the dose delivered to the user by pen 20 and related information are transmitted to smartphone 30 and stored in memory 33 at block 110. In addition to or in lieu of prompting the user at 128 to not use medicine infusion device 70 to administer medicine, medicine infusion device 70 may include a mechanical or software-based safety feature that temporarily locks medicine infusion device 70 to prevent the dispensing of medicine. In this way, medicine over-delivery may be avoided.

As mentioned above, the example approach 100 is merely provided for illustrative purposes and is not intended to be limiting in any way. Other approaches are also contemplated, and such approaches may involve more or fewer operations performed in a different order. For example, some other approaches may include an additional operation between blocks 126 and 116, and the additional operation may be a safety feature that prompts the user to use medicine infusion device 70 to deliver the recommended dose of medicine.

While several aspects of the present disclosure have been detailed above and are shown in the drawings, it is not intended that the disclosure be limited thereto, as it is intended that the disclosure be as broad in scope as the art will allow and that the specification be read likewise. Therefore, the above description and accompanying drawings should not be construed as limiting, but merely as exemplifications of particular aspects. Those skilled in the art will envision other modifications within the scope and spirit of the claims appended hereto.

What is claimed is:

1. A processor-implemented method, comprising:
identifying an amount of medicine for delivery to a patient;
determining a communication path toward a first medicine administration device of a plurality of medicine administration devices in a mesh network, the plurality of medicine administration devices further comprising a second medicine administration device that is prioritized over the first medicine administration device for delivering medicine to the patient; and
when the amount of medicine remains undelivered by the second medicine administration device, causing delivery of the amount of medicine to the patient by the first medicine administration device based on communicating the amount of medicine toward the first medicine administration device via the communication path.

2. The method according to claim 1, wherein the mesh network is a full mesh network.

3. The method according to claim 1, wherein the mesh network is a partial mesh network.

4. The method according to claim 1, wherein the communication path includes a relay node that is communicatively coupled to the first medicine administration device via a different communication path.

5. The method according to claim 1, wherein the first medicine administration device is an insulin infusion device, and wherein the second medicine administration device is an insulin injection device.

6. The method according to claim 1, wherein determining the communication path comprises determining that the first medicine administration device is connected to the mesh network.

7. The method according to claim 1, further comprising:
prior to causing delivery of the amount of medicine, determining that the amount of medicine remains undelivered to the patient by the first medicine administration device.

8. A system comprising:
one or more processors; and
one or more processor-readable storage media storing instructions which, when executed by the one or more processors, cause performance of:
identifying an amount of medicine for delivery to a patient,
determining a communication path toward a first medicine administration device of a plurality of medicine administration devices in a mesh network, the plurality of medicine administration devices further comprising a second medicine administration device that is prioritized over the first medicine administration device for delivering medicine to the patient, and
when the amount of medicine remains undelivered by the second medicine administration device, causing delivery of the amount of medicine to the patient by the first medicine administration device based on communicating the amount of medicine toward the first medicine administration device via the communication path.

9. The system according to claim 8, wherein the mesh network is a full mesh network.

10. The system according to claim 8, wherein the mesh network is a partial mesh network.

11. The system according to claim 8, wherein the communication path includes a relay node that is communicatively coupled to the first medicine administration device via a different communication path.

12. The system according to claim 8, wherein the first medicine administration device is an insulin infusion device, and wherein the second medicine administration device is an insulin injection device.

13. The system according to claim 8, wherein determining the communication path comprises determining that the first medicine administration device is connected to the mesh network.

14. The system according to claim 8, wherein the one or more processor-readable storage media further store instructions which, when executed by the one or more processors, cause performance of:
prior to causing delivery of the amount of medicine, determining that the amount of medicine remains undelivered to the patient by the first medicine administration device.

15. One or more non-transitory processor-readable storage media storing instructions which, when executed by one or more processors, cause performance of:
identifying an amount of medicine for delivery to a patient,
determining a communication path toward a first medicine administration device of a plurality of medicine administration devices in a mesh network, the plurality of medicine administration devices further comprising a second medicine administration device that is prioritized over the first medicine administration device for delivering medicine to the patient, and
when the amount of medicine remains undelivered by the second medicine administration device, causing delivery of the amount of medicine to the patient by the first medicine administration device based on communicating the amount of medicine toward the first medicine administration device via the communication path.

16. The one or more non-transitory processor-readable storage media according to claim 15, wherein the mesh network is a full mesh network.

17. The one or more non-transitory processor-readable storage media according to claim 15, wherein the mesh network is a partial mesh network.

18. The one or more non-transitory processor-readable storage media according to claim 15, wherein the communication path includes a relay node that is communicatively coupled to the first medicine administration device via a different communication path.

19. The one or more non-transitory processor-readable storage media according to claim 15, wherein the first medicine administration device is an insulin infusion device, and wherein the second medicine administration device is an insulin injection device.

20. The one or more non-transitory processor-readable storage media according to claim 15, wherein determining the communication path comprises determining that the first medicine administration device is connected to the mesh network.

* * * * *